United States Patent [19]

Barnes

[11] Patent Number: 4,536,655
[45] Date of Patent: Aug. 20, 1985

[54] FLUOROMETER HAVING AN IMPROVED OPTICAL SYSTEM

[75] Inventor: Clarence W. Barnes, San Francisco, Calif.

[73] Assignee: Axonics, Inc., Mt. View, Calif.

[21] Appl. No.: 527,366

[22] Filed: Aug. 29, 1983

[51] Int. Cl.³ .............................................. G01L 1/20
[52] U.S. Cl. .................................................. 250/461.1
[58] Field of Search ............... 250/461.1, 461.2, 458.1, 250/459.1

[56] References Cited

U.S. PATENT DOCUMENTS 3,854,050 12/1974 Peterson et al. ................. 250/461.2
4,258,264 3/1981 Kotera et al. ..................... 250/484.1
4,394,580 7/1983 Gielisse ............................. 250/461.1

*Primary Examiner*—Alfred E. Smith
*Assistant Examiner*—Richard Hanig
*Attorney, Agent, or Firm*—Flehr, Hohbach, Test, Albritton & Herbert

[57] ABSTRACT

A fluorometer system is disclosed in which a carousel-like system is rotated by a stepper motor to provide a sequence of sample wells to a single optical exciting path. An ultraviolet tube positioned adjacent that path provides an excitation beam which is reflected into common optical path which coincides with the position of the well along the common path is deflected by a beam splitter or the like through an appropriate filtering device to a photomultiplier tube which is located adjacent the common light path on the same side of the path as the ultraviolet tube. The photomultiplier tube is located below the ultraviolet tube to provide a proper direction of convection current.

Further, a solid state photosensor sensitive in red spectrum such as a phototransistor or photodiode is provided adjacent the ultraviolet tube, with a ruby positioned between the ultraviolet tube and the photosensor the take advantage of the fact that solid-state photosensors are especially responsive to light in the red range. The output of the photosensor is fed back to the A to D converter and microprocessor software to take account for the fact that with tube aging or fluctuation in the line current, the output of the ultraviolet tube may vary.

17 Claims, 1 Drawing Figure

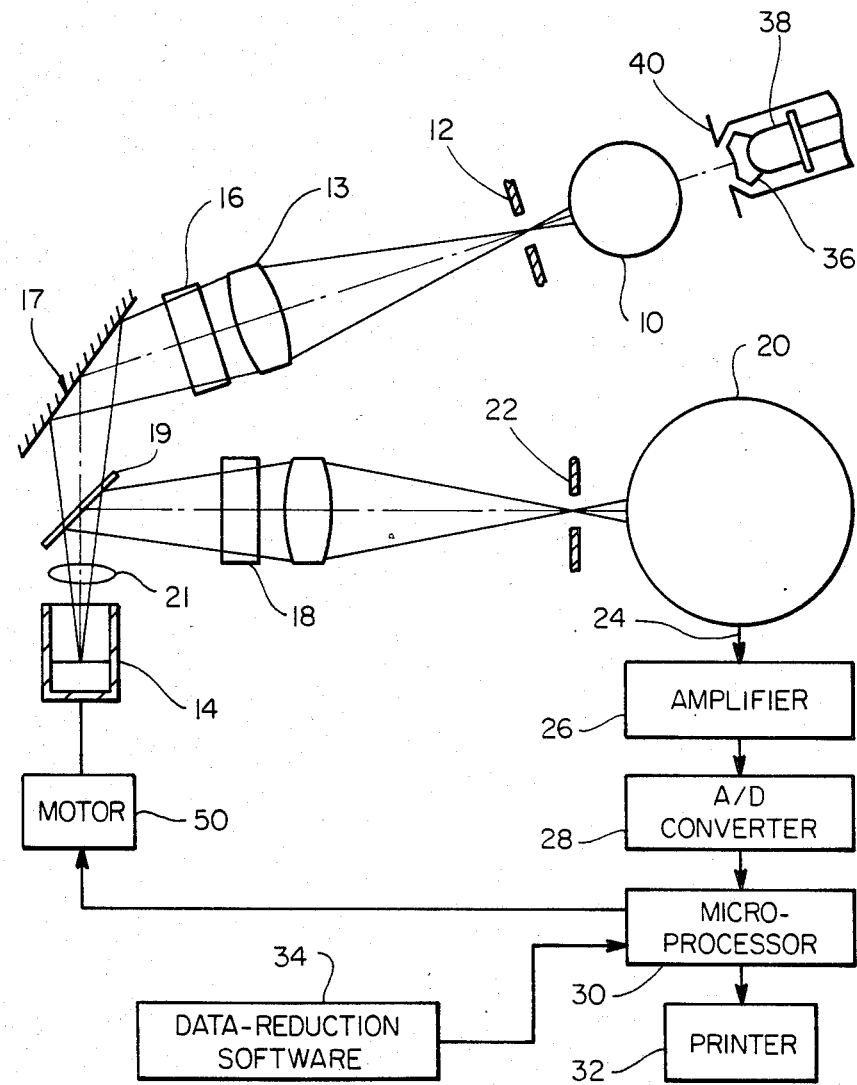
FIG_1

FLUOROMETER HAVING AN IMPROVED OPTICAL SYSTEM

The subject invention is directed to an improved high efficiency fluorometer and comprises a device for determining the relative fluorescence of test samples in miniature polystyrene test wells which are designed for use in fluorescent immuno assays, and especially to the illuminating optical system for this fluorometer.

Fluorometers have been designed and are known for measuring fluorescent levels of samples in a series of tests known as fluorescent immuno assays. Fluorometers have been extensively used to measure the relative fluorescence of light emmitted by samples in wells as an indication of the presence of antibodies in the wells. In a typical application, an ultraviolet lamp projects a beam through a lens to an excitation filter. The excited beam passes the excitation filter and is reflected by a mirror downward into the solution sample well, causing the sample substance to fluoresce. The emitted light passes upward from the well, and is passed through emission filters which are specifically selected to pass light only within a certain band width to a photomultiplier tube. The emitted light is then enhanced, processed and the information comprising relative fluorescent units relative to a base line established by a sample well containing a known substance is then sent to a printer.

Typically, such systems have been very expensive, and only capable of being used by highly trained personnel. One of the major problems with such prior art systems has been the optical system which often consists of a lamp and photomultiplier which must be placed at least 90° apart or on opposite sides of the sample in order to separate the excitation and emission beams. This has lead to complex optical systems of both considerable expense and size.

It is a general object of the present invention to provide a fluorometer which is of a simple construction and expense and size.

It is a general object of the present invention to provide a florometer which is of a simple construction and has great simplicity of use especially by incorporation of a simplified folded optical system which places both the ultraviolet and photomultiplier tubes on the same side and adjacent to the path common to the excitation beam and emitted beam. In such a fluorometer, it is especially important to monitor the radiation output of the ultraviolet tube, as this will inherently affect the level of emissions from the excited substance.

Therefore another object of the present invention is to provide means for consistently and accurately monitoring the output of the ultraviolet tube.

It is yet another objective of the present invention to provide for keeping the ultraviolet tube and photomultiplier tubes cool, as overheating of these tubes and especially the photomultiplier tube will affect the accuracy of the out current of the photomultiplier tube.

These and other objectives and advantages are achieved in amodular low cost, high accuracy fluorometer system in which a carousel-like system is rotated by a stepper motor to provide a sequence of sample wells to a single optical exciting path. An ultraviolet tube positioned adjacent that path provides an excitation beam which is reflected into a common optical path which coincides with the position of the sample well to be read. The light emitted from the sample well along the common path is deflected by a beam splitter or the like through an appropriate filtering device to a photomultiplier tube which is located adjacent the common light path on the same side of the path as the ultraviolet tube. The photomultiplier tube is located below the ultra-violet tube to provide a proper direction of convection current to keep the photomultiplier tube cool and avoid modification of the current output of the photomultiplier tube.

The output of the photomultiplier tube is amplified and converted to a digital level, processed by known data reduction and analysis software and printed out.

The result is a highly efficient and economical fluorometer system.

In a further advantageous improvement, a solid state photosensor sensitive in red spectrum such as a phototransistor or photodiode is provided adjacent the ultraviolet tube, with a ruby positioned between the ultraviolet tube and the photosensor to take advantage of the fact that NPN photosensors are especially responsive to light in the red range. The output of the photosensor is fed back to the analog to digital converter and microprocessor software to take account for the fact that with tube aging or fluctuation in the line current, the output of the ultraviolet tube may vary.

A fluorometer of the present invention may be better understood with reference to FIG. 1 which is a cross-sectional view of the optical system of the fluorometer shown in combination with a block diagram of the basic data analysis elements of the fluorometer.

To briefly summarize the critical elements of the fluorometer shown in FIG. 1, ultraviolet radiation from an ultraviolet lamp 10 passes through a shield 12 and is focused into a sample well 14 after passage through an optical excitation filter 16. This filter selects a narrow band of ultraviolet wavelength suitable for excitation of the fluorescent substance used in the assay contained in the well 14. The fluorescent radiation emitted by the material in the sample well 14 is reflected by a beam splitter 16 into an emission filter 18 where scattered and reflected ultraviolet radiation from the ultraviolet source 10 is rejected. A precisely defined band of longer wave length radiation is passed from the emission filter 18 to the photomultiplier tube 20 via the shield 22.

The intensity of the radiation passing through the emission filter 18 is measured by multiplier tube 20 which provides a current output signal on line 24 proportional to a strength of the light emission received by photomultiplier tube 20. The signal from the photomultiplier tube 20 is amplified by amplifier 26, converted to a digital form at analog to digital converter 28, and sent through a microprocessor 30 where fluorescence levels are computed and temporarily stored. The levels of the critical components in the sample are then computed based upon calibration wells which are also included in the carousel. The thermal printer 32 then prints out a tabulation of fluorescence units for each well in the set. The printer may also print out a correlation coefficient describing how well the calibration data defines a standard calibration curve using the data reduction software incorporated in software package 34.

The techniques of amplification, conversion data reduction and printing are well known in the art and are not described in detail herein.

This invention is especially directed to the arrangement of optical excitation and emission system, and the monitoring system for the output of the ultraviolet tube which consists of the ruby crystal 36, photosensor 38 and shield 40 which monitor the output of the ultraviolet tube. It is well known that once the output of the tube can be accurately monitored, adjustment can be made to the data representing the output of the tube using a formula (photomultiplier tube output)×(constant K/sensor 38 output). Thus, a correction can be incorporated into microprocessor software to account for variations in ultraviolet tube 10 output; alternatively, the output of the photosensor 38 could be used to modify a current controlling circuit reference level to modify the driving current to the ultraviolet tube. A current control system is shown in the patent application of Clarence Barnes entitled Ultraviolet Light Starting and Controlling Circuit, U.S. Ser. No. 527,343, filed 8-29-83 incorporated herein by reference and filed currently with this patent application.

Considering the operation of the system elements in greater detail, the ultraviolet light 10 shines through a shielded opening 12 onto a focusing lens 13 which is of a standard type used to concentrate the light on a linear path so that it will illuminate the liquid or other substance in well 14 as fully as possible. The light output having passed through the focusing lens 13 passes through an excitation filter 16. This filter 16 is essentially a band-pass filter which selectively passes light at a wavelength at about 365 nanometers. The reason for selection of this wavelength to be passed is that it is found that light at this wavelength reacts best with the sample in the well to cause fluorescence. Use of such an excitation filter is necessary because ultraviolet lamps put out light at a plurality of wavelengths.

The light is then deflected by a mirror 17 at an angle of about 55° and passes through a beam splitter 19 to impinge on the well 14 to cause the substance in the well to fluoresce. The beam splitter itself is of a type found in the art which allows the light from the ultraviolet source 10 to pass along the path from mirror 17 to sample well 14 along the common path 21. However, light from the sample caused by fluorescence of the sample in response to the impinging ultraviolet which returns along the common path 21 from sample well 14 to beam splitter 19 is reflected at an acute angle of about 45° to the same side of the common path as the ultraviolet light source 10 is located, on through an emission filter 18 and concentrating lens 19 to a photo-multiplier 20.

The emission filter is selected to pass radiation at a wavelength of at about 450 nanometers. This wavelength is selected because it has been found that certain substances excited by light at a wavelength 365 nanometers puts out light at a wavelength which is optimum for measurement purposes at about 450 nanometers. For testing of other chemical substances, filters that pass other wavelengths of light need to be used.

The light is then concentrated by concentrating lens 19 to be focused by a shield 22 onto photomultiplier 20. This photomultiplier in turn puts out a current which is proportional to the intensity of the radiation of the sample. That is, the more anitbodies or the like that are being measured, the more fluorescence that occurs.

It should be noted that, of course, to the extent that the ultraviolet light output weakens with age the level of light impinging the substance to be measured would be somewhat reduced. It is therefore important to monitor the level of the light output from the ultraviolet tube. For this purpose, the photosensor 38 is used to monitor the radiation output of the ultraviolet light 10. Since photosensors have in fact been used in the past; however, they are not sensitive in the ultraviolet end or blue end of the light spectrum. Therefore, a solid-state photosensor which is sensitive to the red end of the light spectrum is utilized;* and in a departure from the past practices, a ruby 36 is interposed between the ultraviolet lamp 10 and the red sensitive sensor 38. By utilizing this, an output curve is developed which constantly represents the level of the radiation output of the ultraviolet light 10. This same output may be fed to amplifier 26 for conversion by analog to digital converter 28. Therefore, either the software may be modified to take account of the reduced light level output from the ultraviolet light; or, alternatively, drive current to the ultraviolet light may be increased to provide a greater light output using a control circuit such as is disclosed in the co-pending application of Clarence Barnes entitled Ultraviolet Light Starting and Maintaining Circuit, filed concurrently with this patent application.

*In some applications it is desirable to interpose an optical filter between the ruby and the UV lamp It should be noted that a shield 40 is further provided surrounding the ruby and the photosensor 38. This is provided to shield the sensor and the epoxy which binds the ruby to the sensor from direct impingement of ultraviolet light. Thus, reflected light does not affect the accuracy of the measurement made by the photosensor.

As noted above, the samples are carried in wells 14, a plurality of such wells being grouped in a carousel which is more fully disclosed in the application of Eric Mitzner et al entitled Microtitvation Carousel Ser. No. 527,607, filed 8-29-83, incorporated herein by reference. This carousel is driven by stepper motor 50 of a type well known in the art and controlled in accordance with well known principles by the microprocessor 30. Thus, the microprocessor in response to receipt and analysis of data from the substance in one well will cause movement of the stepper motor to position the next well 14 in the common light path under arrow 17 and the splitter 18. In addition to providing samples to be tested certain wells may be reference wells i.e. flouresce at known levels to check the correlation of the whole system.

Other modifications of the invention disclosed herein may become apparent to a person skilled in the art after review of the subject patent application. Therefore, the scope of this invention is intended to be limited only by the scope of the claims which follow:

What is claimed is:

1. A low profile optical sensing system for an ultraviolet energized fluorescent light responsive device wherein ultraviolet light is imaged on a selected one of a plurality of samples carried in sample wells, the wells defining a sample plane, the ultraviolet light passing along a first light path, wherein fluorescent light emanating from said selected sample is detected along a second lignt path which in part is in common with said first light path, the sensing system comprising:
   an ultraviolet tube located to the side of said common light path above said sample plane,
   a fluorescence detector located on the same side of said light path and between the ultraviolet tube and the sample plane, and
   means defining one end of said common path for passing ultraviolet rays from a source of said ultraviolet light to said sample along said common path,
   and means reflecting said fluorescent light to said fluorescence responsive device.

2. An optical sensing system as claimed in claim 1 further comprising an ultraviolet detector adjacent said ultraviolet tube, and feedback means coupled to said light detector to control the output from said tube.

3. An optical sensing system as claimed in claim 1 wherein said ultraviolet detector comprises a photosensor for converting light impinging thereon to electrical energy, and means located between said photosensor and said sample to limit the light falling on the sample to the red light spectrum.

4. A system as claimed in claim 3 where said ruby is fastened to the front surface of said photosensor.

5. A system as claimed in claim 4 further comprising shield means surrounding said ruby and sensor for reducing the incidence of ambient light on said sensor.

6. A system as claimed in claim 5 further comprising a stepping motor for selectively positioning said samples on said carousel relative to said optical path.

7. A system as claimed in claim 1 further comprising filter means in said first light path to fully illuminate said sample.

8. A system as claimed in claim 1 wherein said means defining one end of said optical path comprises a beam splitter for passing light from said ultraviolet source and reflecting light to said detector.

9. A system as claimed in claim 1 wherein said beam splitter is positioned at an angle of about 45° relative to said common path.

10. A system as claimed in claim 1 wherein said means for defining a first path further comprises an optical filter for selectively passing light from said fluorescent light source at an optimum frequency for reacting with said sample.

11. A system as claimed in claim 1 wherein said means for defining a second optical path further comprises an optical bandpass filter for selectively passing light from said fluorescing substance.

12. In an optical sensing system for a device wherein substances carried individually into a sensing path in wells of a carousel defining a sample plane are caused to fluoresce at a first given wavelength by exposing them to light at a second given wavelength, an improved folded optical system comprising:
  a source of ultraviolet light located to the side of said sensing path,
  excitation filter means for selectively directing certain wavelengths of said ultraviolet light on said substance,
  means for reflecting said ultraviolet light at a first acute angle onto said sensing path,
  receiver means located on the same side of said sensing path as said light source responsive to emissions from said sample to generate a current proportional to radiation from said sample,
  means for selectively reflecting fluorescence from said sample to said receiver at a second angle more acute than said first angle, said receiver being located between the light source and the sample plane whereby a folded, low profile optical system is provided.

13. The improvement of claim 12 wherein said means for selectively relfecting comprises a beam splitter which is transparent to light from said ultraviolet light source but reflects light fluorescing from said substance.

14. The improvement of claim 12 wherein said excitation filter means comprises a bandpass filter for selectively passing light at a frequency of about 365 nanometers.

15. The improvement of claim 12 wherein said photomultiplier tube is located substantially directly below said ultraviolet light source.

16. The improvement of claim 12 further comprising emission filter means for selectively passing light at a frequency of about 450 nanometers.

17. The improvement of claim 12 further comprising a light responsive device for monitoring the light output from said ultraviolet light source, and
  means interposed between said ultraviolet light and said light responsive device for providing primarily light in the red spectrum to said sample and said light responsive device.

* * * * *